US00PP37708P2

(12) United States Plant Patent
Meyer

(10) Patent No.: US PP37,708 P2
(45) Date of Patent: Sep. 22, 2026

(54) ***HEMEROCALLIS* PLANT NAMED 'Gothic Grenadine'**

(50) Latin Name: ***Hemerocallis* (L.) hybrid**
Varietal Denomination: Gothic Grenadine

(71) Applicant: Chris Meyer, Zeeland, MI (US)

(72) Inventor: Chris Meyer, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 19/729,002

(22) Filed: Jan. 14, 2026

(51) Int. Cl.
*A01H 5/02* (2018.01)
*A01H 6/00* (2018.01)

(52) U.S. Cl.
USPC ..... Plt./312

(58) Field of Classification Search
USPC ..... Plt./312
See application file for complete search history.

(56) References Cited

U.S. PATENT DOCUMENTS

PP32,364 P2 * 10/2020 Meyer ..... A01H 6/00
Plt./312

* cited by examiner

*Primary Examiner* — Susan McCormick Ewoldt
*Assistant Examiner* — Zachariah Allan Kay

(57) ABSTRACT

A new and distinct *Hemerocallis* plant named 'Gothic Grenadine' characterized by winter-hardy compact habit with clean, dark-green, semi-evergreen foliage. The vigorous tetraploid plant produces a high number of strong, upright, four to seven-way branched scapes with numerous, large, single, flowers that are rounded, fragrant, very dark red, with a ruffled piecrust edging, and yellow to light green throat beginning in mid-July for about four weeks.

1 Drawing Sheet

Botanical classification: *Hemerocallis* (L.) hybrid.
Variety denomination: 'Gothic Grenadine'.

STATEMENT REGARDING PRIOR DISCLOSURES UNDER 37 CFR 1.77(B)(6)

On Feb. 1, 2025, a photograph and brief description of *Hemerocallis* 'Gothic Grenadine' were placed on a website of Walters Gardens, Inc. and on Jun. 3, 2025, the new plant was advertised in the "Walters Gardens 2025-2026 Catalog". The first sale of the new plant was made by Walters Gardens, Inc. to DJ's Greenhouse & Gardens, Country Arbors Nursery, and Bemis Farms Nursery on Feb. 3, 2025. Walters Gardens, Inc. obtained the new plant and all information relating thereto, from the inventor. No plants of *Hemerocallis* 'Gothic Grenadine' have been sold, in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to a new and distinct daylily plant, *Hemerocallis* 'Gothic Grenadine' hereinafter also referred to as the new plant or just the cultivar name 'Gothic Grenadine'. *Hemerocallis* 'Gothic Grenadine' was hybridized by the inventor, Chris Meyer, in the spring of 2011 in a greenhouse at a wholesale perennial nursery in Zeeland, Michigan, USA. The new plant originated from a breeding program conducted by the inventor with the specific intention to improve the garden worthiness, expand color regimens and increase flowering period which were some of the criteria of further trials in the trial beds at the same nursery in Zeeland, MI. The female or seed parent was a proprietary hybrid between 'Apache War Dance' (not patented) and 'Desert Flame' (not patented) known by the breeder code 07-1342-1 (not patented) and the male or pollen parent was 'Desire of Nations' (not patented).

The new plant was selected as a single seedling from this cross, and during confidential evaluations in a trial bed beginning in 2012 at the same nursery was assigned the breeder code 11-607-3. The new plant has been asexually propagated by division at the same wholesale nursery in Zeeland, MI since 2014 with all resultant asexually propagated plants having retained all the same unique traits as the original plant. *Hemerocallis* 'Gothic Grenadine' is stable and reproduces true to type in successive generations of asexual reproduction.

There are nearly 110,000 registered daylilies with The American *Hemerocallis* Society, which is the International Cultivar Registration Authority for the genus *Hemerocallis*. The new plant is distinct from the parents and all cultivars known to the inventor.

The female parent has an orangish-red flower color and the scapes were taller. The male parent has flowers that are a grape/cranberry blend, a frosted bluish-lavender eye and dark lavender gold filigree edge a with a yellow to green throat on a slightly shorter scape.

The most similar daylily cultivars known to the inventor are 'Alexander Cook' (not patented), 'Blood Countess' (not patented), 'Chocolate Ruffles' (not patented), 'Clive Platman Memorial' (not patented), 'Crimson Guard' (not patented), 'Galactic Blast' (not patented), 'Harry McClurg' (not patented), 'JP's Drachenfels' (not patented), 'Kens Em' (not patented), 'Life's Journey' (not patented), 'Old Glory Flies' (not patented), 'Pavlik' (not patented), 'Prince of Thieves' (not patented), 'Alexander Cook' has flowers that purplish-red with a darker purplish-red halo and yellow throat, and the tepals are not as broad. 'Blood Countess' has red flowers, a thin picotee margin and yellowish-green throat on shorter scapes. 'Chocolate Ruffles' in a diploid with slightly smaller flowers of burgundy red with a white edge and yellowish-green throat. 'Clive Platman Memorial' has larger flowers with crispate tepals of dark blood red with a thin gold edge and midribs on taller scapes. 'Crimson Guard' has taller scapes with lighter red flowers having a lime green throat. 'Galactic Blast' has a much taller scape and flowers with more yellow throat and more intensely sinuate yellow tepal margins. 'Harry McClurg' has dormant foliage, the scapes are taller and the flowers are lighter red with more triangular yellow throat. 'JP's Drachenfels' has dormant foliage with taller scapes, and the flowers are lighter red with more triangular greenish-yellow throat and yellow midribs, and the tepals are more reflexed. 'Kens Em' has taller scapes with flowers that have a yellow throat and narrower and flatter tepals. 'Life's Journey' has dormant foliage, taller scapes, flowers with more reflexed tepals and lighter reddish color. 'Old Glory Flies' has dormant foliage, taller scapes, nocturnal flowers of lighter red with less crisped margins and narrower tepals. 'Pavlik' has a lighter reddish flower on taller scapes and dormant foliage. 'Prince of Thieves' has dormant foliage, much taller scapes, and flowers that are lighter red with a whitish-red watermark eye.

*Hemerocallis* 'Gothic Grenadine' differs from all other daylilies known to the applicant, by the combination of the following traits:

1. Winter-hardy, compact habit with clean, dark-green, semi-evergreen foliage;
2. Fragrant, single, limbate, rounded flowers about 13.9 cm wide of very dark red with a ruffled piecrust edge and yellow to light green throat;
3. Inner and outer tepals slightly reflexed;
4. Plants produce four to seven-way branched scapes of about 59 cm tall with up to 30 flowers per scape;
5. Flowering begins about mid-July with excellent coverage for about four weeks;
6. Plant is vigorous and tetraploid producing numerous upright scapes.

BRIEF DESCRIPTION OF THE DRAWINGS

The drawing of the new plant demonstrates the overall appearance of the plant, including the unique traits. The colors are as accurate as reasonably possible with color reproductions. Ambient light spectrum, temperature, source and direction may cause the appearance of minor variation in color.

The drawing shows a close-up of flowers and buds.

DETAILED BOTANICAL DESCRIPTION

The following descriptions and color references are based on the 2015 edition of The Royal Horticultural Society Colour Chart except where common dictionary terms are used. The new plant, *Hemerocallis* 'Gothic Grenadine', has not been observed under all possible environments. The phenotype may vary slightly with different environmental conditions, such as temperature, light, fertility, moisture and maturity levels, but without any change in the genotype. The following observations and size descriptions are of a three-year-old plant in a sunny landscape at a display garden in Zeeland, Michigan with supplemental water and fertilizer.

Botanical classification: *Hemerocallis* (L.) hybrid;

Parentage: Female (seed) parent is 07-1342-1; male (pollen) is 'Desire of Nations';

Propagation: Division of the rhizome;

Growth rate: Moderate to rapid;

Crop time: About 8 to 10 weeks to flower starting in spring in a 3.8-liter container from vernalized one-year-old plant;

Rooting habit: Fleshy, about 2.5 mm diameter; lightly branching;

Root color: Nearest RHS 159C depending on soil type;

Plant shape and habit: Winter-hardy herbaceous perennial with four basal shoots emerging from rhizomes producing a radially symmetrical mound of arching leaves;

Ploidy level: Tetraploid;

Plant size: Foliage height about 80 cm tall from soil line to the top of the leaves, about 140 cm wide at the widest point; flowering to about 78 cm tall;

Leaves: Semi-evergreen; linear; apex narrowly acute; base sheathing, sessile; entire; glabrous, slightly glaucous abaxial and adaxial; folded, equitant, basal; about 13 leaves per division;

Leaf aspect: Arching in outer leaves to erect in inner leaves;

Leaf size: To about 130 cm long and 4.5 cm across, average about 120 cm long and about 3.5 cm across;

Cauline leaves: About 2 per scape about one-third of the way up the peduncle to flowers; reduced, to about 15 cm long and 3 cm wide, average about 5.5 cm long and 1.7 cm wide;

Leaf color: Cauline and basal young abaxial nearest RHS 144A, adaxial between RHS 144A and RHS 146B; mature cauline and basal leaves adaxial between RHS 137B and RHS 138A, abaxial nearest RHS 137B;

Veins: Parallel; color adaxial nearest RHS NN137B and abaxial nearest RHS NN137B;

Flower description:

Flowers: Funnelform; single, with two sets of three tepals; zygomorphic, incomplete; diurnal; aspect upward and outwardly; about 13.5 cm across and 9.1 cm tall to exserted stigma, corolla about 7.5 cm deep; corolla tube diameter at fusion about 1.2 cm, length from base to fusion point about 1.8 cm long; individually lasting for about one day; peduncle remains effective from mid-July into early-August for approximately four weeks in Zeeland, Michigan with into late summer;

Inflorescence: Upwardly, erect; stiff; glaucous; glabrous; heavily branched to about 78 cm tall and flowering to about 15 cm across; with 4 to 7 branches and to about 30 flowers;

Flower fragrance: None detected;

Buds about one day prior to opening: Oblong ellipsoid; bluntly acute apex and tepals beginning to separate, proximal 1.7 cm narrowed terete; base rounded; about 8.8 cm long and about 2.5 cm in diameter at widest point with proximal 1.7 cm narrowing to about 0.9 cm diameter;

Bud color one day from opening: Narrowed base nearest RHS N144D, proximal portion of inflated bulb portion nearest RHS 151C, distal portion of inflated bulb between RHS 178C and RHS 178B except dorsal tepal midrib between RHS 15B and RHS 15C, apical 2 mm nearest 137C;

Tepals: 2 sets of 3;

Inner tepals: Broadly ovate; glabrous; rounded apex; base truncate, fused in proximal 1.8 cm; with moderate narrow margin undulation; midrib fluted about 2 mm wide on abaxial and costate on adaxial surface; opening to nearly flat face; width at fusion about 8 mm, about 5.5 cm across at widest point and about 10 cm long;

Outer tepals: Ovate; glabrous; rounded apex; base truncate, fused in proximal 1.8 cm; flat; midrib not obvious; opening to nearly flat face; width at fusion about 1 cm, about 3.3 cm across at widest point and 10 cm long;

Inner tepal color: Adaxial distally between RHS 187A and RHS 186C, proximal throat nearest RHS N144A in the center and proximal margins nearest RHS 10C, basal midrib nearest RHS 10B; abaxial distal 1 mm to 2 mm wide margin nearest RHS N186A, nearest RHS 183B in the distal two-thirds with the center marbled with RHS 183B and RHS 11A, proximal one-quarter nearest RHS 11A with a thin proximal margin nearest RHS 11B;

Outer tepal color: Adaxial distal three-quarters between RHS 187A and RHS 186C, proximal throat nearest RHS N144A in the center and proximal margins nearest RHS 10C; abaxial distal 2 mm nearest RHS 137C, distal two-thirds marbled with nearest RHS 183C and RHS 16B and in the proximal one-third nearest RHS 151B and proximal margins nearest RHS 11B;

Pedicel: Cylindrical; glabrous; slightly lustrous; from 5 mm to 15 mm long and 4 mm to 6 mm diameter; subtended by bract; aspect upward to slightly outwardly;

Pedicel color: Nearest RHS 137C;

Bract: Broadly ovate; with acute apex and truncate semi-clasping base; to 3 cm long and 2.4 cm wide, decreasing in distal branches and flowers; subtending branches and flowers;

Bract color: Adaxial distal portion between RHS 138B and RHS 138C, adaxial proximal portion between RHS 145B and RHS 145C, abaxial distal portions between RHS 143A and RHS 143B, abaxial proximally between RHS 145D and RHS 145C;

Peduncle: Cylindrical; glabrous; slightly glaucous; to 19 per plant during peak initial flowering, average about 13 peduncles per plant; repeating, producing a second set after the first set is done flowering; erect to about 78 cm tall and 2 cm diameter at base, average about 74 cm tall and 1.6 cm diameter; extending just above foliage; 4 to 7 branches; to 30 flowers, average about 22 per peduncle;

Peduncle color: Between RHS 144A and RHS 138B;

Gynoecium: Single; tri-carpelled; glabrous; about 9.1 cm long;

*Style*.—Single; cylindrical; about 8.2 cm long, 1 mm diameter before stigma and 2 mm diameter at base, arcuate slightly upward at distal one-third; color distally marbled with nearest RHS 183C and RHS 16C, middle nearest RHS 16C, and proximally nearest RHS 4C.

*Stigma*.—Globose; 1 mm diameter; color nearest RHS 160D.

*Ovary*.—Conical; smooth; acute apex, truncate base; about 8 mm long and 4 mm diameter at base; color nearest RHS 145B.

Androecium: Six; glabrous;

*Filaments*.—Six; cylindrical distally, slightly applanate proximally; lustrous; arcuate upward in distal one-third; adnate to inner tepal in basal 21 mm above ovary; free in distal 56 mm long from fusion point on tepal; to about 77 mm long, 3.5 mm across and 2 mm thick near tepal attachment, and 1 mm diameter at anther; color where fused with adaxial corolla nearer RHS 151D than RHS 150C, distally nearest RHS 183A, center nearest RHS 16A, and proximally above fusion nearest RHS 10B.

*Anthers*.—Oblong; dorsifixed, longitudinal; about 7 mm long and 2 mm wide; color nearest RHS N186A.

*Pollen*.—Abundant; less than 0.1 mm long; color nearest RHS 17A.

Fruit and seeds: Not observed, but fertility has not been tested;

Disease and pest resistance and tolerance: 'Gothic Grenadine' has not shown resistance to diseases and pests beyond that common for daylilies, and given the northern testing regions the new plant has not been exposed to daylily rust, *Puccinia hemerocallidis*. The plant grows best and shows best coloration with fertile soil, plenty of moisture, and adequate drainage, but is able to tolerate some drought when mature and direct sun without leaf burn when provided sufficient water. The flower is very tolerant of high sun exposure for such a dark color.

Hardiness at least from USDA zone 3 through 9, and other disease resistance and tolerance is typical of that of other daylilies. The new plant is useful for landscaping en masse, as a single specimen or small groups.

I claim:

1. A new and distinct ornamental daylily plant named *Hemerocallis* 'Gothic Grenadine' as herein described and illustrated.

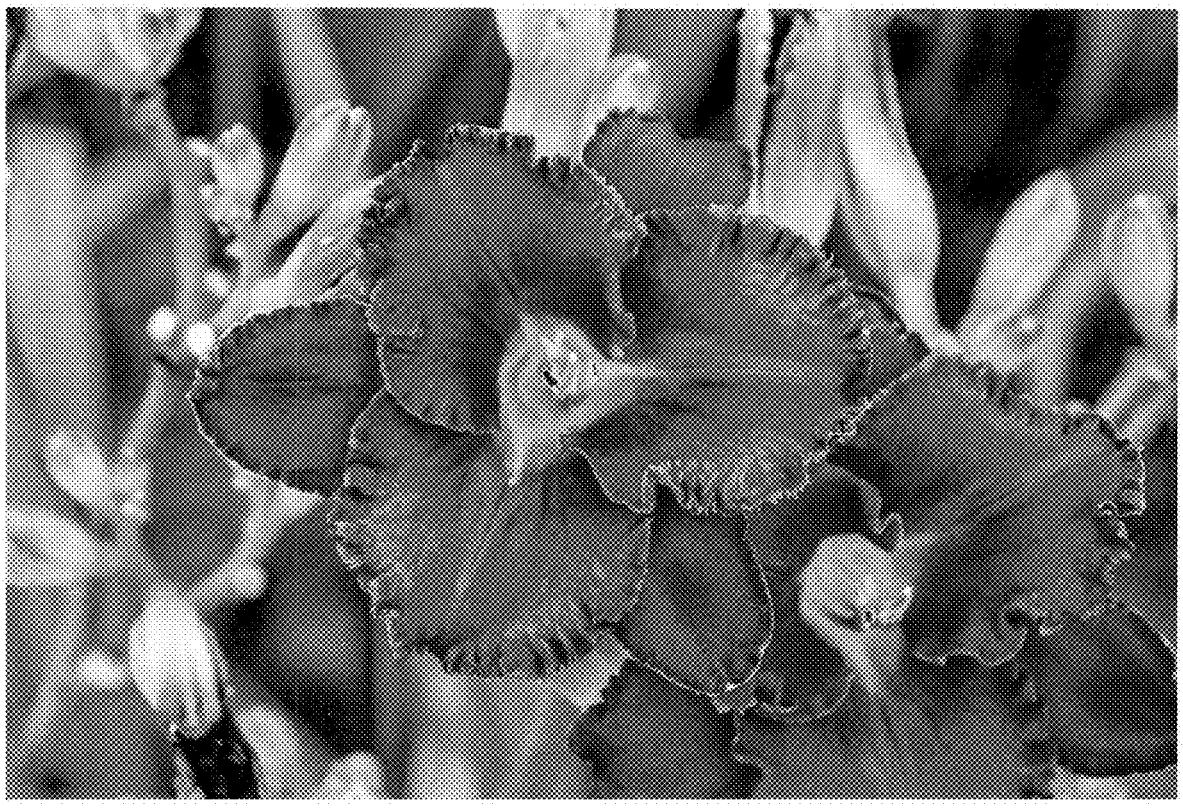

* * * * *